United States Patent [19]

Lord et al.

[11] Patent Number: 4,703,118
[45] Date of Patent: Oct. 27, 1987

[54] SYNTHESIS OF 3-IODOMETHYL CEPHALOSPORINS

[75] Inventors: Gary E. Lord, West Lafayette; Robert M. Metzler; David D. Wirth, both of Lafayette, all of Ind.

[73] Assignee: Eli Lilly and Company, Indianapolis, Ind.

[21] Appl. No.: 720,643

[22] Filed: Apr. 8, 1985

[51] Int. Cl.$^4$ .................... C07D 501/38; A61K 31/54
[52] U.S. Cl. ................................. 540/224; 540/215; 540/225; 540/219
[58] Field of Search .................. 544/16, 225; 540/224, 540/215

[56] References Cited

U.S. PATENT DOCUMENTS

| | | | |
|---|---|---|---|
| 4,258,041 | 3/1981 | O'Callaghan et al. | 424/246 |
| 4,266,049 | 5/1981 | Bonjouklian | 544/16 |
| 4,336,253 | 6/1982 | Lunn et al. | 424/246 |
| 4,369,313 | 1/1983 | Jones et al. | 544/24 |
| 4,379,787 | 4/1983 | Lunn et al. | 424/246 |
| 4,382,931 | 5/1983 | Lunn et al. | 424/246 |
| 4,382,932 | 5/1983 | Lunn et al. | 424/246 |
| 4,388,316 | 6/1983 | Lunn et al. | 424/246 |
| 4,396,620 | 8/1983 | Lunn et al. | 424/246 |
| 4,406,898 | 9/1983 | Lunn et al. | 424/246 |

FOREIGN PATENT DOCUMENTS

| | | |
|---|---|---|
| 27705 | 11/1984 | Australia . |
| 74268 | 3/1983 | European Pat. Off. . |
| 3316798 | 11/1984 | Fed. Rep. of Germany . |
| 2105334 | 3/1983 | United Kingdom . |
| 2106905 | 4/1983 | United Kingdom . |
| 2106906 | 4/1983 | United Kingdom . |

OTHER PUBLICATIONS

Bonjouklian et al. "Reactions of TMSI with Cephalosporin Esters", *Tetrahedron Letters*, vol. 22, No. 40, 3915–3918, (1981).

*Primary Examiner*—Nicholas S. Rizzo
*Attorney, Agent, or Firm*—Bruce J. Barclay; Leroy Whitaker

[57] ABSTRACT

The present invention provides a process for preparing a 3-iodomethyl cephalosporin by treating a bis(trialkylsilyl)-7-amino-4-carboxylic acid-3-substituted cephalosporin derivative with a trialkylsilyl iodide derivative.

10 Claims, No Drawings

SYNTHESIS OF 3-IODOMETHYL CEPHALOSPORINS

BACKGROUND OF THE INVENTION

U.S. Pat. No. 4,266,049 teaches a process for converting a 3-(alkanoyloxy or carbamoyloxy)cephalosporin to the corresponding 3-iodomethyl cephalosporin with a trialkylsilyl iodide. This process requires separate blocking of the 4-carboxylic acid and 7-amino substituents prior to the reaction.

The present process permits the synthesis of 3-iodomethyl cephalosporins from a bis(trialkylsilyl)-7-amino-4-carboxylic acid starting material. Since separate blocking of the 7-amino and 4-carboxylic acid substituents is not necessary, the synthesis of 3-iodomethyl cephalosporins in fewer steps is now possible. Further, the present process permits the synthesis of the desired compounds in higher yields than previously possible. These advantages are significant when preparing large quantities of 3-iodomethyl cephalosporins which are intermediates for clinically active compounds. In addition, the present process permits the introduction of any desired acyl group at the 7-position of the cephalosporin ring without separate blocking or deblocking steps.

SUMMARY OF THE INVENTION

The present invention relates to a process for preparing 3-iodomethyl cephalosporins. More specifically, it relates to a process for preparing a 3-iodomethyl cephalosporin of the formula

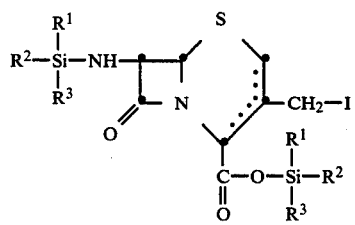

I which comprises reacting a compound of the formula

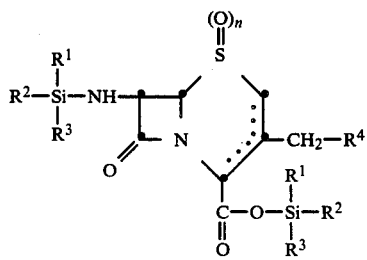

II with a trialkylsilyl iodide of the formula

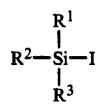

in an aprotic solvent under substantially anhydrous conditions at a temperature in the range of about $-20°$ C. to about $35°$ C., wherein each of $R^1$, $R^2$ and $R^3$ independently is $C_1$–$C_3$ alkyl; $R^4$ is $C_1$–$C_4$ alkanoyloxy or a carbamoyloxy group of the formula

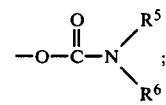

each of $R^5$ and $R^6$ independently is hydrogen or $C_1$–$C_3$ alkyl; and n is 0 or 1.

The present invention also provides a compound of the formula

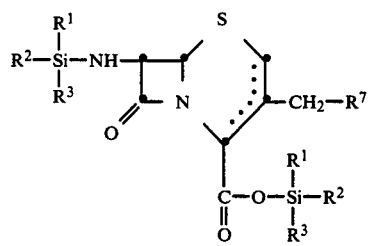

III wherein:
each of $R^1$, $R^2$ and $R^3$ independently is $C_1$–$C_3$ alkyl; and $R^7$ is iodo or

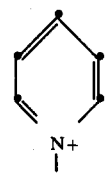

having an associated anion $A^-$.

DETAILED DESCRIPTION OF THE INVENTION

Temperatures shall be reported herein as degrees Celsius. Quantities shall be reported herein as weight units, except for liquids, which are reported in volume units.

As used herein, the term $C_1$–$C_s$ alkyl represents a straight or branched alkyl chain having from one to three carbon atoms. $C_1$–$C_3$ Alkyl groups are methyl, ethyl, n-propyl and isopropyl.

$C_1$–$C_4$ Alkanoyloxy represents a straight or branched alkanoyl chain having from one to four carbon atoms and having an oxygen atom between the alkanoyl chain and another bond. Exemplary $C_1$–$C_4$ alkanoyloxy groups include formyloxy, acetoxe, propionoxy, butyroxy, and the like.

While the full range of variables described herein for the present process are believed operable, certain variables are preferred. For example, each of $R^1$, $R^2$ and $R^3$ is preferably methyl and n is 0. Further, $R^4$ is preferably acetoxy. Other preferred aspects of the present invention exist and will be noted hereinafter.

The dotted bonding lines between the 2, 3, and 4-positions of the dihydrothiazine ring indicate that the double bond may exist in either the 2-position or the 3-position. Accordingly, when a 2-cephem compound represented by formula II is employed in the process of this invention, a 3-iodomethyl-2-cephem compound of formula I is formed. When a 3-cephem compound is employed as the starting material, which is preferred, the product represented by formula I is a 3-iodomethyl-3-cephem derivative.

The starting material employed in the present process may exist as either the sulfide or sulfoxide form. As shown in the reaction scheme above when n=1 in formula II, the sulfoxide group of the starting material is reduced to provide the 3-iodomethyl cephalosporin in the sulfide form represented by formula I. As will be readily understood, when starting with the sulfide form n=0, the sulfide form of the molecule is obtained.

As described above, the present invention relates to a process for preparing a 3-iodomethyl cephalosporin comprising reacting a 3-alkanoyloxymethyl or 3-carbamoyloxymethyl substituted cephalosporin having trialkylsilyl groups at the 7-amino and 4-carboxylic acid positions with a trialkylsilyl iodide. The present process is represented by the following reaction scheme:

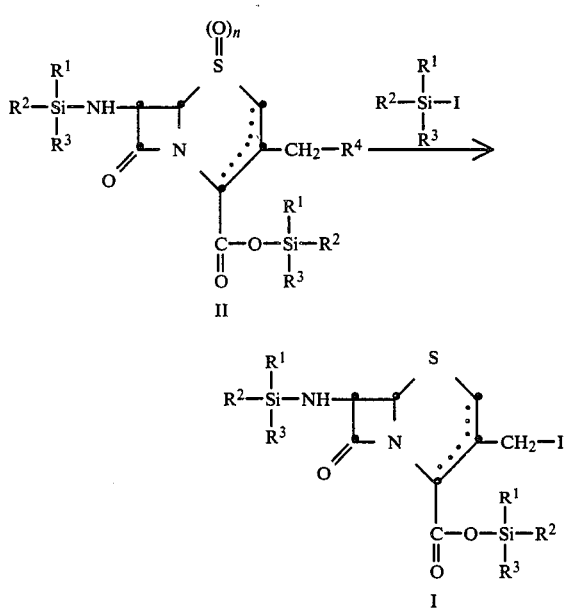

wherein $R^1$, $R^2$, $R^3$, $R^4$ and n are as defined above.

Typical trialkylsilyl iodide starting materials employed in the present process include trimethylsilyl iodide (TMSI), triethylsilyl iodide, tri-n-propylsilyl iodide, methyl diethylsilyl iodide, dimethyl ethylsilyl iodide, methyl ethyl n-propylsilyliodide and the like. The preferred trialkylsilyl iodide for use herein is trimethylsilyl iodide.

The trialkylsilyl iodides employed in the process of this invention are prepared by normal procedures and are highly reactive substances. While trimethylsilyl iodide is preferred because of its reactivity, the higher trialkylsilyl iodides are less reactive in the present process and thus necessitate the use of longer reaction times to achieve the desired yield of the product. Typically, the trialkylsilyl iodide is either commercially available or readily prepared under anhydrous conditions by treating a hexaalkyldisilane with iodine to afford the trialkylsilyl iodide in situ. Also, a trialkylsilyl chloride or bromide compound can be reacted with sodium iodide to afford the corresponding trialkylsilyl iodide derivative.

A variety of aprotic solvents may be employed in the present process. Typical aprotic solvents include the chlorinated hydrocarbon solvents such as chloroform, methylene chloride, 1,2-dichloroethane, 1,1,2-trichloroethane, 1,1,2,2-tetrachloroethane, and like chlorinated hydrocarbon solvents; aromatic hydrocarbons, such as benzene, toluene and the xylenes; organonitriles, for example acetonitrile and propionitrile; nitroalkanes such as nitromethane and nitroethane; and sulfones, for example sulfolane. In general, the solvents employed in the present process can be any convenient solvent which solubilizes the cephalosporin starting material and which is unreactive with the trialkylsilyl iodide reagent.

The process of the present invention is carried out under substantially anhydrous conditions. The term "substantially anhydrous conditions", as used herein, represents reaction conditions which are virtually free from water and an oxygen atmosphere due to the reactivity of trialkylsilyl iodide with water. Accordingly, solvents are preferably dried prior to use in the present invention and the trialkylsilyl iodide is kept moisture free prior to its use. Further, it is preferred that all reaction vessels be thoroughly dried prior to their use, for example by flame or heat drying. It is also preferred that the process be carried out in an inert atmosphere, such as under nitrogen or argon gas.

In the present process, one mole equivalent of the trialkylsilyl iodide reacts with one mole equivalent of the starting material of formula II. However, the trialkylsilyl iodide reagent can also reduce cephalosporin sulfoxides to the corresponding sulfide derivative independent of its function as an iodinating agent. As such, when n=1 in formula II, an additional mole equivalent of the trialkylsilyl iodide reagent is required. Preferably, a mole equivalent excess of the silyl iodide reagent is used for best yields in the present process.

The present process is preferably conducted in the presence of an amine acid scavenger in order to remove any acid which may be present in the reaction mixture. For example, hydrogen iodide may exist by virtue of there being a slight molar excess of the trialkylsilyl iodide present in the reaction medium or trace amounts of acid in the reagent. Exemplary amine acid scavengers for use in the present process include pyridine, polyvinylpyridine, N-methylmorpholine, trialkylamines such as triethylamine, and N,N-dialkylanilines such as N,N-dimethylaniline, and especially N,N-diethylaniline (DEA).

The process of the present invention is substantially complete after about 10 minutes to about 12 hours when conducted at a temperature in the range of about −20° C. to about 35° C. Preferably, the reaction is conducted for about 30 minutes to about 120 minutes at a temperature of about 0° C. to about 10° C.

The compounds prepared by the present process are useful intermediates to a variety of cephalosporin derivatives. In particular, the compounds are useful in the synthesis of ceftazidime, (6R,7R)-3-(1-pyridiniummethyl)-7-[(Z)-2-(carboxyprop-2-oxyimino)-2-(2-aminothiazol-4-yl)acetamido]ceph-3-em-4-carboxylate, as taught in U.S. Pat. No. 4,258,041, and ceftazidime pentahydrate, as taught in U.S. Pat. No. 4,329,453.

The compounds prepared by the present process are preferably reacted with pyridine to provide the corresponding 3-pyridinium derivatives, which are finally hydrolyzed to afford (6R,7R)-7-amino-3-(1-pyridiniummethyl)ceph-3-em-4-carboxylic acid dihydrochloride dihydrate, which is also known as 1-[(7-amino-2-carboxy-8--oxo-5-thia-1-azabicyclo[4.2.0-]oct-2--en-3-yl)methyl]pyridinium chloride monohydrochloride dihydrate, hereinafter termed 3-pyridinium cephalosporin nucleus. The scheme for this reaction is as follows:

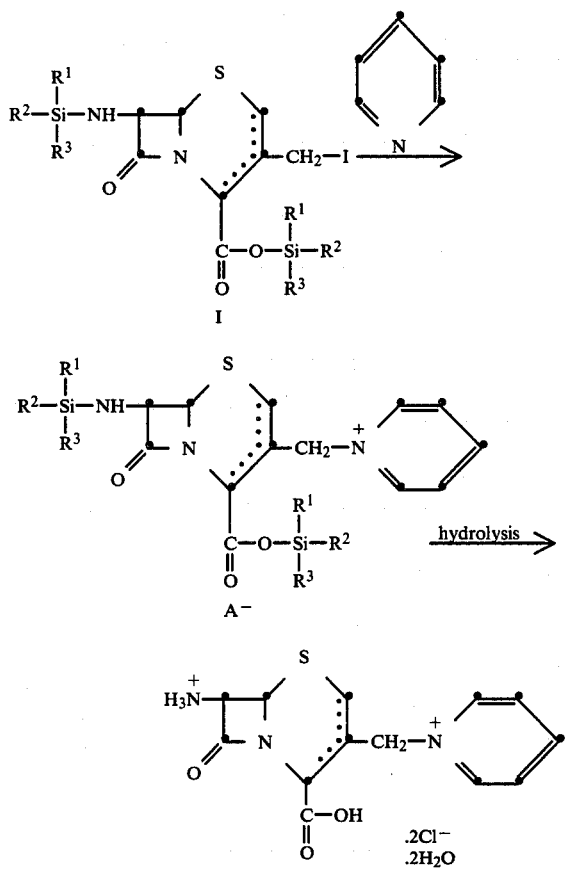

The first step of the above process is typically conducted without isolating the compound of formula I which acts as the starting material. Generally, at least an equimolar amount of pyridine is added to the reaction mixture, with amounts of up to two mole equivalents of pyridine or more preferred. The reaction is typically conducted at a temperature in the range of about 0° C. to about 30° C., more preferably from about 10° C. to about 20° C., for a period of time in the range of about 30 minutes to about 24 hours, more typically in the range of about 1 hour to about 6 hours. The compound of the invention thus prepared is typically not isolated but rather converted to 3-pyridinium cephalosporin nucleus.

If it is desired to isolate the compounds of formula III wherein $R^7$ is pyridinium they will have an associated anion $A^-$. This anion may be derived from either an inorganic or organic acid. Exemplary inorganic acids from which anions may be derived include the hydrohalic acids such as hydrochloric acid, hydrobromic acid or hydroiodic acid, as well as phosphoric acid and sulfuric acid. Typical organic acids from which anions may be derived include the sulfonic acids such as p-toluenesulfonic acid, p-bromophenylsulfonic acid and methanesulfonic acid, oxalic acid, carbonic acid, succinic acid, citric acid, acetic acid and benzoic acid. These compounds of formula III may be readily prepared by procedures well known to those of ordinary skill in the art.

The trialkylsilyl groups on the compound thus prepared are finally hydrolyzed by the addition of an aqueous alcoholic solvent and suitable acid to afford 3-pyridinium cephalosporin nucleus. Typical alcoholic solvents include isopropanol, ethanol and especially methanol. Suitable acids for use include the hydrohalic acids such as hydrobromic or especially hydrochloric acid, as well as carboxylic acids such as acetic acid, sulfonic acids such as methanesulfonic acid, and phosphoric acid. The reaction is conducted at a temperature in the range of about 0° C. to about 30° C. for a period of about 30 seconds to about 24 hours. The reaction is preferably carried out at a temperature between about 15° C. and about 20° C. for about 1 minute to about 2 hours. The crystalline product is typically isolated by the addition of a polar solvent such as methanol, ethanol, isopropanol, acetone and especially acetonitrile to the mixture, followed by vacuum filtration.

The trialkylsilyl groups of the compound of formula I may also be hydrolyzed directly without the addition of pyridine to provide a valuable intermediate having a 3-iodomethyl substituent. This hydrolysis step is conducted in the same manner as that described above.

It will be readily apparent to one of ordinary skill that instead of hydrolyzing the compound of formula I, or its 3-(1-pyridiniummethyl) derivative, either compound may be acylated directly prior to hydrolysis according to standard procedures.

In the synthesis of the starting material employed in the present process two mole equivalents of the trialkylsilyl moiety react with the 7-amino and 4-carboxylic acid moieties of the cephalosporin nucleus to provide the corresponding compound of formula II having the following structure:

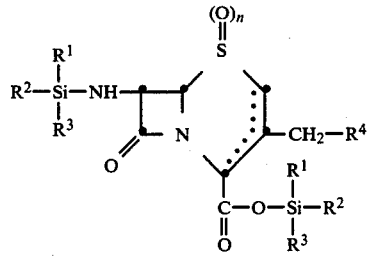

wherein $R^1$, $R^2$, $R^3$, $R^4$ and n are as defined above.

Silylation of 7-aminocephalosporanic acid derivatives with a variety of silylation reagents is known. For example, the reader is directed to U.K. Patent No. 1,269,697 for a discussion of the silylation of 7-aminocephalosporanic acid with N,O-bis(trimethylsilyl)acetamide, trimethylsilyl urea and other reagents, and EPO No. 43,630 for a discussion of silylation with hexamethyldisilazane employing a saccharine catalyst.

Suitable silylation reagents will contain at least one silyl moiety to which three $C_1$-$C_3$ alkyl groups are bound. Exemplary silylation reagents include the trialkylsilyl iodides hereinbefore defined, as well as trialkylsilyl bromides, such as trimethylsilyl bromide, trialkylsilyl chlorides, such as trimethylsilyl chloride, hexaalkyldisilazanes, such as 1,1,1,3,3,3-hexamethyldisilazane, bis(trialkylsilyl)ureas, such as 1,3-bis(trimethylsilyl)urea, and other like silylation reagents. Sufficient silylation reagent is added to the reaction medium so as to sufficiently block both positions of the starting cephalosporin nucleus. Typically, at least 2.0 molar equivalents of silylation reagent are required for each molar equivalent of cephalosporin starting material. For bis-silyl reagents, at least 1.0 molar equivalent of silylation reagent is required for each molar equivalent of cephalosporin starting material.

The silylation is conducted at a temperature in the range of about −10° C. to about 60° C. for a period of about 1 to about 24 hours.

The silylation may be conducted in the presence of an acid scavenger which functions to remove any acid which is present in the reaction mixture as a by-product of the silylation step. Also, acid may exist by virtue of there being a slight molar excess of the silylation reagent present in the reaction medium or trace amounts in the reagent. Preferably, the acid scavenger employed will be the same compound employed in the present process, an amine acid scavenger.

The compounds used to prepare the cephalosporin starting materials of formula II are known compounds readily prepared by prior art processes. The preferred compound is 7-aminocephalosporanic acid (7-ACA) represented by the following formula:

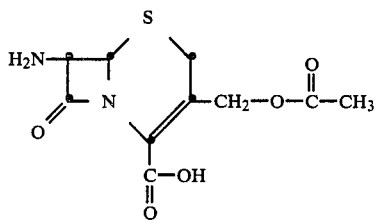

wherein $R^4$ of formula II is acetoxy.

The following Examples further illustrate the process of the present invention. The Examples are not intended to be limiting to the scope of the invention in any respect and should not be so construed.

In the following Examples, the structure and purity of 3-pyridinium cephalosporin nucleus was determined by a high pressure liquid chromatographic comparison to an authentic reference standard as follows. The sample to be analyzed was isolated from the reaction mixture as a solid. A liquid chromatograph with a UV detector at 254 nm was injected with 10 μl of a solution of the sample dissolved in the solvent system used as the column eluent. The column eluent was 5% methanol:95% ion pair solution (v:v), the ion pair solution being prepared by dissolving 1.0 g of pentanesulfonic acid sodium salt and 5 ml of phosphoric acid in 1 l of water. The column had a 25 cm×4.6 mm I.P. of Spherisorb ODS (Regis Chemical Co.). The flow rate was 1.0 ml per minute.

While the compounds prepared by the present process were not isolated, the structure of the compound of formula I wherein each of $R^1$, $R^2$ and $R^3$ was methyl and the double bond was in the $\Delta^3$ position, termed 3-(iodomethyl)-7-[(trimethylsilyl)amino]-3-cephem-4-carboxylic acid, trimethylsilyl ester was verified by obtaining a $^{13}C$ NMR spectra of the compound in situ. The compound was prepared as follows: trimethylsilyl iodide was prepared by adding 0.76 ml (0.0037 mol) of hexamethyldisilane to a slurry of 0.94 g (0.0037 mol) of iodine in 1 ml of methylene chloride. The solution was stirred for 90 minutes and added to a slurry of 0.5 g (0.0018 mol) of 7-aminocephalosporanic acid in 1.5 ml of deuterated methylene chloride containing 0.88 ml (0.0055 mol) of N,N-diethylaniline at about 5° C. The solution was stirred at about 5° C. for about 1 hour under nitrogen and filtered through a glass wool plug into a 10 cm NMR tube. A $^{-}C$ NMR was conducted employing a spectrometer at about 0° C. to afford the following values for the desired compound: δ from external $(CH_3)_4Si$; 5.4 (C3′), 26.9 (C2), 59.8, 63.3 (C6, C7), 123.6 (C3), 127.1 (C4), 168.3, 160.7, 171 (C8, C10 carboxyl), and carbonyl of trimethylsilyl acetate). Additional non-ceph peaks were at 9.8 and 50.8 ($CH_3$ and $CH_2$ of DEA) 137.9, 114.3, 129.3, 126.1 (aromatic, DEA) 21.8 ($CH_3$ on trimethylacetate).

The following procedure was used to prepare a compound of formula III wherein $R^7$ is pyridinium, $R^1$, $R^2$ and $R^3$ are methyl and the double bond forms the $\Delta^3$ isomer, termed 1-[[8-oxo-7-[(trimethylsilyl)amino]-2-[[trimethylsilyl)oxy]carbonyl]-5-thia-1-azabicyclo[4.2.0]-oct-2-en-3-yl]methyl]pyridinium. The compound was prepared as follows: trimethylsilyl iodide was prepared by combining 29.83 ml (0.146 mol) of hexamethyldisilane and 37.0 g (0.146 mol) of iodine in methylene chloride. The resulting mixture was refluxed for about 30 minutes and cooled to about 10° C. The mixture was added to a slurry of 23.56 g (0.087 mol) of 7-aminocephalosporanic acid and 33.65 ml (0.212 mol) of N,N-diethylaniline in about 80 ml of methylene chloride over a period of about 20 minutes while maintaining the temperature of the mixture below about 10° C. The mixture was stirred for about 3 hours at about 3° C. and an additional 3.00 ml of trimethylsilyl iodide was added. The reaction mixture was stirred for about 45 minutes at about 5° C. and 9.45 ml of pyridine was added. The mixture was stirred for about 2 hours at about 20°–25° C. to provide 1-[[8-oxo-7-[(trimethylsilyl)amino]-2-[[(trimethylsilyl)oxy]carbonyl]-5-thia-1-azabicyclo[4.2.0]oct-2-en-3-yl]methyl]pyridinium in situ. The structure of the compound was verified by proton NMR in methylene chloride to provide the following results: δ from external $(CH_3)_4Si$; 0.2 (9H, $(CH_3)_3SiN$), 0.4 (9H, $(CH_3)_3SiO$) 3.4 (1H, d, J=18 Hz, C2) 4.0 (1H, d, J=18 Hz, C2), 4.8 (1H, d, J=5 Hz, C6 or C7) 5.0 (1H, d, J=5 Hz, C6 or C7), 5.7 (1H, d, J=14 Hz, C3′) 6.1 (1H, d, J =14 Hz, C3′), 7.5 (m, 2H, β pyridine), 8.1 (1H, m, γ pyridine), 8.6 (m, 2H, α pyridine).

The compound 3-pyridinium cephalosporin nucleus exists as the dihydrochloride dihydrate salt. Therefore, all assay calculations for the free base of that compound are based on the maximum of 73% available free base in a reference standard. Further, all percent yield calculations for 3-pyridinium cephalosporin nucleus are uncorrected for the purity of that compound.

EXAMPLE 1

To a 250 ml 3-neck round bottom flask was added 90 ml of methylene chloride, 40.26 g (0.159 mol) of iodine and 23.22 g (0.159 mol) of hexamethyldisilane. The resulting mixture was refluxed for approximately 30 minutes under nitrogen and cooled to room temperature to afford trimethylsilyl iodide in situ.

To a 500 ml 3-neck round bottom flask was added 80 ml of methylene chloride and 22.66 g (0.0801 mol) of 96.2% pure 7-aminocephalosporanic acid under nitrogen. To this slurry was added 31.56 g (0.212 mol) of N,N-diethylaniline. While maintaining the temperature of the mixture below approximately 25° C., the trimethylsilyl iodide solution prepared above was added dropwise to the mixture over a period of approximately 1 hour. The resulting mixture was stirred for approximately 75 minutes at about 20°–25° C. and 7.0 g (0.089 mol) of pyridine was added to the mixture. The reaction mixture was stirred for about 2½ hours at 20°–25° C. and 45 ml of methanol and 29.6 g of hydrochloric acid was added. The mixture was stirred for 2 hours at 20°–25° C. To the mixture was added 60 ml of acetonitrile and the resulting mixture was seeded with a crystal of the desired product. An additional 60 ml of acetonitrile was added over a period of approximately 60 minutes and the resulting mixture was stirred overnight. The precipitated solid was collected by filtration and washed with a solution of 12.5 ml of methanol and 110 ml of acetonitrile. The solid was next washed with 50 ml of acetonitrile to provide 20.15 g of the product, 3-pyridinium cephalosporin nucleus, as a light yellow solid. The purity of the solid was 57%. Yield 62.9%.

EXAMPLE 2

To a 125 ml single-neck round bottom flask equipped with a magnetic stirrer and reflux condenser was added 32 ml of methylene chloride, 19.8 g (0.078 mol) of iodine and 11.42 g (0.078 mol) of hexamethyldisilane under nitrogen. The contents of the reaction vessel were allowed to stir under self-heat to reflux. The mixture was cooled to room temperature when the exotherm ended to afford trimethylsilyl iodide in situ.

A 250 ml 3-neck round bottom flask fitted with a mechanical stirrer, addition funnel and thermometer was charged with 30 ml of methylene chloride and 10 g (0.037 mol) of 7-aminocephalosporanic acid under a nitrogen atmosphere. The mixture was cooled to a temperature of about 0°–5° C. and 19.18 g (20.4 ml, 0.129 mol) of N,N-diethylaniline was added thereto. While maintaining the temperature of the reaction mixture between about 0° C. and about 6° C., the trimethylsilyl iodide solution prepared above was added dropwise to the reaction mixture. The addition funnel was rinsed with 4 ml of methylene chloride and the resulting mixture was stirred for 60 minutes at about 0° C. to about 5° C. The reaction mixture was charged with 6.54 g (6.69 ml, 0.083 mol) of pyridine. A cold water bath was placed around the reaction vessel in order to maintain the temperature of the mixture at about 14° C. to about 18° C. for about 2 hours. The reaction mixture was cooled to about 5° C. and a solution of 20 ml of methanol and 10 ml of hydrochloric acid at a temperature of about 5° C. was added to the mixture over a period of about 30 seconds. The mixture was next charged with 40 ml of acetonitrile and the reaction mixture was seeded with a crystal of the desired product. Next, 30 ml of acetonitrile was added to the mixture over a period of about 60 minutes at a temperature of about 20°–25° C. The reaction mixture was allowed to stir overnight at 20°–25° C. and the precipitated solid was collected by filtration. The resulting solid was washed with a solution of 7 ml of methanol and 45 ml of acetonitrile. The solid was dried under vacuum at a temperature in the range of about 25°–40° C. overnight to provide 8.45 g of 3-pyridinium cephalosporin nucleus having a purity of 67% by assay. Yield 57.1%.

EXAMPLE 3

The trimethylsilyl iodide solution used in Examples 3–6 was prepared as follows. To a 500 ml 3-neck round bottom flask was added 78.36 g (0.309 mol) of iodine and 126 ml of methylene chloride. To this solution was added 45.17 g (0.309 mol) of hexamethyldisilane under a nitrogen atmosphere so as to maintain a gentle reflux. The reaction mixture was allowed to cool to room temperature following the addition of the reagent to afford trimethylsilyl iodide in situ.

A 250 ml 3-neck round bottom flask was charged with 10.27 g (0.037 mol) of 97.4% pure 7-aminocephalosporanic acid and 30 ml of methylene chloride under a nitrogen atmosphere. The mixture was cooled to approximately 0°–5° C. and 19.19 g (0.129 mol) of N,N-diethylaniline was added. The resulting mixture was stirred for approximately 58 minutes and cooled to 0°–5° C. Next, 70.61 g (0.147 mol) of the trimethylsilyl iodide solution prepared above was added to the reaction mixture dropwise while maintaining the temperature at about 0°–6° C. Following addition of the trimethylsilyl iodide solution, the reaction mixture was stirred for approximately 1 hour. To this mixture was added 6.54 g (0.083 mol) of pyridine, and the reaction mixture was warmed to 14°–18° C. and stirred for about 2 hours. The mixture was cooled rapidly to 0°–5° C. and 30 ml of a chilled solution of methanol:concentrated HCl (2:1, v:v) was added dropwise over a period of approximately 30 seconds. The reaction mixture was stirred for a few minutes following the removal of the external ice bath and 40 ml of acetonitrile was added. The mixture was seeded with a crystal of the desired product and 30 ml of acetonitrile was added dropwise. The mixture was stirred overnight and the precipitated solid was collected by vacuum filtration. The resulting solid was washed with 52 ml of a solution of methanol:acetonitrile (7:45, v:v). The solid was dried under vacuum to provide 11.64 g of 3-pyridinium cephalosporin nucleus as a solid having a purity of 66.6%. Yield 78.6%.

EXAMPLE 4

Following the general procedure of Example 3, 10.32 g (0.038 mol) of 7-aminocephalosporanic acid and 30 ml of methylene chloride in the presence of 19.28 g (0.129 mol) of N,N-diethylaniline was treated with 70.94 g (0.148 mol) of the trimethylsilyl iodide solution prepared in Example 3 under a nitrogen atmosphere. The resulting compound was reacted with 6.58 g (0.083 mol) of pyridine to provide 11.95 g of 3-pyridinium cephalosporin nucleus having a purity of 66.3%. Yield 78.6%.

EXAMPLE 5

Following the general procedure outlined in Example 3, 10.3 g (0.038 mol) of 7-aminocephalosporanic acid in 30 ml of methylene chloride and in the presence of 19.25 g (0.129 mol) of N,N-diethylaniline was treated with 70.79 g (0.147 mol) of the trimethylsilyl iodide solution prepared in Example 3 under nitrogen. The resulting compound was reacted with 6.56 g (0.083 mol) of pyridine to provide 11.69 g of product, 3-pyridinium cephalosporin nucleus, as a solid having a purity of 66.6%. Yield 76.9%.

EXAMPLE 6

Following the general procedure outlined in Example 3, 10.27 g (0.038 mol) of 7-aminocephalosporanic acid in 30 ml of methylene chloride and in the presence of 19.19 g (0.129 mol) of N,N-diethylaniline was treated with 70.59 g (0.146 mol) of trimethylsilyl iodide solution prepared according to the procedure in Example 3 under a nitrogen atmosphere. The resulting compound was reacted with 6.54 g (0.083 mol) of pyridine to provide 11.65 g of 3-pyridinium cephalosporin nucleus having a purity of 66.8%. Yield 76.6%.

EXAMPLE 7

To a slurry of 19.86 g (0.078 mol) of iodine in 32 ml of methylene chloride was added 11.43 g (0.078 mol) of hexamethyldisilane under nitrogen at a sufficient rate so as to maintain reflux. When the addition was complete, the solution was stirred for 45 minutes while cooling to room temperature. This solution was added dropwise to a slurry of 10.49 g (0.039 mol) of 7-aminocephalosporanic acid and 19.16 g (0.129 mol) of N,N-diethylaniline in 30 ml of methylene chloride under nitrogen while maintaining the temperature of the slurry between about 0° C. and about 5° C. The mixture was stirred for two hours at about 0°–5° C. To the reaction mixture was added 6.60 g (0.084 mol) of pyridine. The reaction mixture was heated to about 14°–17° C., stirred for two hours and cooled to about 0°–5° C. A cooled solution of 20 ml of methanol and 10 ml of concentrated hydrochloric acid was added to the reaction mixture followed by the addition of 35 ml of acetone at room temperature over one hour to crystallize the product. The reaction mixture was stirred for 15 hours at room temperature and filtered. The resulting solid was washed with 25 ml acetone to provide 12.68 g of 3-pyridinium cephalosporin nucleus having a purity of 68.7% as determined by assay. Yield 81.3%.

EXAMPLE 8

A slurry of 10.81 g (0.04 mol) of 7-aminocephalosporanic acid in 70 ml of methylene chloride was charged with 12.2 ml (0.096 mol) of trimethylsilyl chloride under nitrogen. To the slurry was added 10.5 ml (0.096 mol) of N-methylmorpholine over 15 minutes while maintaining the temperature of the reaction mixture between about 20° C. and about 24° C. The mixture was stirred at room temperature for approximately 30 minutes and 70 ml of diethyl ether was added dropwise to the mixture over 30 minutes. The resulting mixture was stirred at room temperature for 30 minutes and the precipitated solid was collected by vacuum filtration. The solid was washed with 50 ml of diethyl ether:-methylene chloride (1:1, v:v) and dried in a vacuum oven overnight to provide 11.68 g of a pale yellow solid. The filtrate from above was concentrated under vacuum to provide an oil. The residual oil was dissolved in 50 ml of methylene chloride and the resulting solution was concentrated under vacuum to provide an oil. The oil was transferred to a 250 ml three-neck round bottom flask and combined with 50 ml of methylene chloride. The resulting solution was cooled to about 0° C. Trimethylsilyl iodide was prepared in situ by the reaction of 7.28 g (0.029 mol) of iodine and 5.85 ml (0.029 mol) of hexamethyldisilane in 20 ml of methylene chloride at reflux for 1 hour under nitrogen. The cooled reaction mixture of 7-[(trimethylsilyl)amino]-cephalosporanic acid, trimethylsilyl ester was charged with 3 ml (0.019 mol) of N,N-diethylaniline and the trimethylsilyl iodide solution from above was added dropwise over 2 minutes under nitrogen. The resulting mixture was stirred for 40 minutes and an additional 1.6 ml of trimethylsilyl iodide was added. The solution was stirred for 50 minutes and 5.55 ml (0.069 mol) of pyridine was added thereto. The mixture was stirred for 2 hours at 17° C. and subjected to the hydrolysis conditions as described above in Example 7 to provide 12.12 g of 3-pyridinium cephalosporin nucleus having a purity of 68 0%. Yield 75.8%.

EXAMPLE 9

A solution of trimethylsilyl iodide was prepared by heating a solution of 7.41 g (0.029 mol) of iodine and 5.96 ml (0.029 mol) of hexamethyldisilane in 20 ml of methylene chloride for 30 minutes at the reflux temperature of the reaction mixture under a nitrogen atmosphere. The solution was cooled to about 5° C. and added to a solution of 14.14 g (0.034 mol) of 7-[(trimethylsilyl)amino]cephalosporanic acid, trimethylsilyl ester in 50 ml of methylene chloride and 2.7 ml (0.017 mol) of N,N-diethylaniline at about 0° C. in a 250 ml three-neck round bottom flask under nitrogen. The resulting mixture was cooled to about 2° C. and stirred at that temperature for 40 minutes. An additional 0.5 ml of trimethylsilyl iodide was added to the mixture which was stirred for an additional 20 minutes at 2° C. The reaction mixture was charged with 4.94 ml (0.061 mol) of pyridine, warmed to about 15° C., and stirred for 2 hours. The mixture was cooled to about 0° C. and a solution of 10 ml of concentrated hydrochloric acid and 20 ml of methanol was added rapidly to the reaction mixture. The mixture was next charged with 30 ml of acetonitrile and seeded with a crystal of the desired product. The mixture was charged with an additional 30 ml of acetonitrile dropwise over 30 minutes and stirred at room temperature for 2 hours. The precipitated solid was collected by vacuum filtration and dried in vacuo at 40° C. for 4 hours to provide 10.92 g of 3-pyridinium cephalosporin nucleus as a tan solid having a purity of 67.2%. Yield 80.3%.

EXAMPLE 10

A solution of 10.0 g (0.037 mol) of 7-aminocephalosporanic acid in 60 ml of methylene chloride was charged with 0.34 g (0.0019 mol) of saccharin and 15.5 ml (0.074 mol) of hexamethyldisilazane in a 250 ml round bottom flask fitted with a mechanical stirrer, condenser and nitrogen inlet tube. The resulting mixture was heated at reflux for approximately 3 hours under nitrogen and cooled to 0° C. A solution of trimethylsilyl iodide was prepared by heating a solution of 6.07 g (0.024 mol) of iodine and 4.9 ml (0.024 mol) of hexamethyldisilane at the reflux temperature of the reaction mixture in 25 ml of methylene chloride for 1 hour under nitrogen. The resulting solution was cooled to room temperature and added in one portion to the 7-[(trimethylsilyl)amino]cephalosporanic acid, trimethylsilyl ester mixture held at a temperature in the range of about 0° C. to about 5° C. The resulting mixture was stirred for about 2 hours at 0°–10° C. and 5.9 ml (0.073 mol) of pyridine was added. The mixture was stirred for 2 hours at 15°–17° C. and concentrated under vacuum. The resulting residue was stored overnight at about 0° C. Residual solvents were removed by the application of vacuum for 1 hour to provide 29.9 g of residue. The residue was dissolved in 50 ml of methylene chloride at room temperature and added in one portion to a solution of 21.72 g (0.037 mol) of Z-2-(2-t-butoxycarbonyl-prop-2-oxyimino)-2-(2-tritylaminothiazol-4-yl)acetyl chloride in 100 ml of methylene chloride under nitrogen. The resulting mixture was cooled to about 0° C. and stirred for 5 minutes. The solution was cooled to about −5° C. and 3 ml of triethylamine was added slowly. The mixture was charged with 50 ml of water and the pH of the solution was raised to about 5.5 with triethylamine. An additional 50 ml of water was added followed by 85 ml of N,N-dimethylacetamide. The solution was stirred for 10 minutes and allowed to warm to room temperature. The solution was decolorized with a 7% solution of sodium thiosulfate. The mixture was shaken for 2 minutes and the layers were separated. The lower layer was transferred to a 1 l. flask and combined with 200 ml of ethyl acetate, 100 ml of diethyl ether and 100 ml of N,N-dimethylacetamide, and seeded with a crystal of the expected product. The solution was stirred overnight at ambient temperature. The resulting slurry was cooled to about 5° C. for 45 minutes and the precipitated solid was collected by vacuum filtration and washed with a solution of 20 ml of ethyl acetate and 20 ml of N,N-dimethylacetamide and finally with 25 ml of ethyl acetate. The resulting solid was dried in vacuo at 40° C. for 6 hours to provide 11.91 g of (6R,7R)-3-(1-pyridiniummethyl)-7-[(Z)-2-(t-butoxycarbonylprop-2-oxyimino)- 2-(2-tritylaminothiazol-4-yl)acetamido]ceph-3-em-4-carboxylate. Yield 33%. Assay 86.6%. An additional 39% of the desired product was present in the mother liquor as determined by HPLC analysis to provide a total yield of 72%.

The structure and purity of the product was identified by a high pressure liquid chromatographic comparison with an authentic reference standard. The liquid chromatograph had a UV detector at 254 nm and a column type of 25 cm × 4.6 mm I.O. Ultrasphere ODS. The column eluent was a solution consisting of 49.4% water, 45% tetrahydrofuran, 5% acetonitrile, 0.5% phosphoric acid and 0.1% triethylamine by volume. The flow rate was 1.5 ml per minute. The amount of solution injected was 10 μl.

The following procedure was used to prepare 3-pyridinium cephalosporin nucleus according to the process of the present invention on a large industrial scale setting.

EXAMPLE 11

To a clean, dry 500 gallon tank was added 250 l. of dry methylene chloride and 170 kg (669.3 mol) of iodine under a nitrogen atmosphere. While maintaining the nitrogen atmosphere, 98 kg (671.2 mol) of hexamethyldisilane was added to the mixture over a period of about 45 to 60 minutes while maintaining the temperature of the mixture in the range of about 25°–35° C. The resulting solution of trimethylsilyl iodide was stirred for approximately 90 minutes at 28°–33° C. and the contents of the reaction vessel were cooled to about −5°–0° C.

A second dry 500 gallon tank was charged with 225 l. dry methylene chloride and 91 kg (334.6 mol) of dry 7-aminocephalosporanic acid under nitrogen. The contents of the tank were cooled to a temperature between 0°–5° C. and 160 l. (150 kg, 1006.7 mol) of N,N-diethylaniline was added to the mixture. While maintaining the temperature of the mixture between 0°–5° C., the trimethylsilyl iodide solution prepared above was added to the mixture. The mixture was stirred for approximately 2 hours. To the mixture was added 53 kg (670.9 mol) of pyridine and the mixture was warmed to a temperature of about 14°–17° C. for a period of about 150 minutes. The reaction mixture was transferred to a 500 gallon tank containing 200 l. of methanol and 110 kg of hydrochloric acid at a temperature of about 10°–15° C. To the mixture was added 300 l. of acetonitrile and a seed of the expected product. The mixture was next charged with an additional 300 l. of acetonitrile over a period of about 60 to 90 minutes. The mixture was agitated for about 8 hours at a temperature between 20°–25° C. The precipitated crystals were collected by centrifugation. The tank was rinsed with a solution of 500 l. of acetonitrile and 50 l. of methanol. The solid was washed with the above solution and with 100 l. of acetonitrile. The resulting crystals were dried in a rotary glass-lined dryer under vacuum at 30°–40° C. until the water content of the crystals was between 8% and 9% by weight to provide 108 kg of 3-pyridinium cephalosporin nucleus having a purity of 67.5%. Yield 80.7%.

We claim:

1. A process for preparing a 3-iodomethyl cephalosporin of the formula

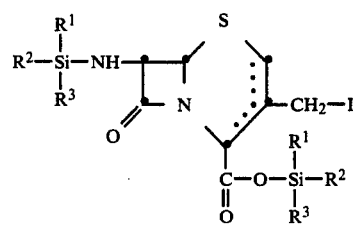

which comprises reacting a compound of the formula

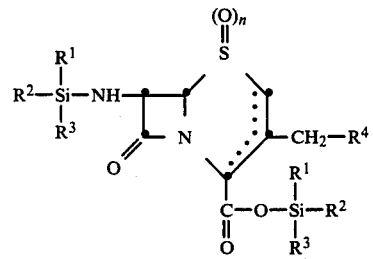

with a trialkylsilyl iodide of the formula

in an aprotic solvent under substantially anhydrous conditions at a temperature in the range of about −20° C. to about 35° C., wherein each of $R^1$, $R^2$ and $R^3$ independently is $C_1$–$C_3$ alkyl; $R^4$ is $C_1$–$C_4$ alkanoyloxy or a carbamoyloxy group of the formula

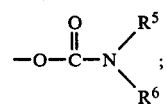

each of $R^5$ and $R^6$ independently is hydrogen or $C_1$–$C_3$ alkyl; and n is 0 or 1.

2. A process of claim 1 wherein each of $R^1$, $R^2$ and $R^3$ is methyl.

3. A process of claim 2 wherein the double bond in the cephem ring system is located in the 3-position.

4. A process of claim 3 wherein $R^4$ is acetoxy.

5. A process of claim 1 wherein the aprotic solvent is methylene chloride.

6. A process of claim 1 wherein the reaction is carried out at a temperature in the range of about 0° C. to about 10° C.

7. A compound of the formula

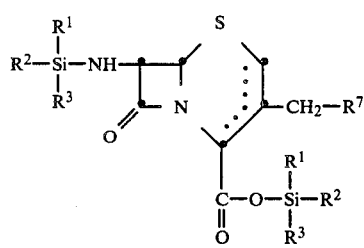
wherein:
each of $R^1$, $R^2$ and $R^3$ independently is $C_1$–$C_3$ alkyl;
and
$R^7$ is iodo or
III 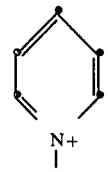
having an associated anion $A^-$.
8. A compound of claim 7 wherein each of $R^1$, $R^2$ and $R^3$ is methyl.
9. A compound of claim 8 wherein $R^7$ is iodo.
10. A compound of claim 8 wherein $R^7$ is
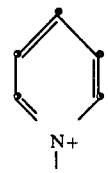
and $A^-$ is halide.
* * * * *